(12) United States Patent
Simon et al.

(10) Patent No.: US 10,470,901 B2
(45) Date of Patent: Nov. 12, 2019

(54) USER CONTROLLED POWER DISCONNECT MECHANISM FOR HUMAN EXOSKELETON

(71) Applicant: STEERING SOLUTIONS IP HOLDING CORPORATION, Saginaw, MI (US)

(72) Inventors: Daniel C. Simon, Freeland, MI (US); Eric D. Pattok, Frankenmuth, MI (US); Patrik M. Ryne, Midland, MI (US)

(73) Assignee: Steering Solutions IP Holding Corporation, Saginaw, MI (US)

( * ) Notice: Subject to any disclaimer, the term of this patent is extended or adjusted under 35 U.S.C. 154(b) by 818 days.

(21) Appl. No.: 15/009,935

(22) Filed: Jan. 29, 2016

(65) Prior Publication Data

US 2016/0220395 A1 Aug. 4, 2016

Related U.S. Application Data

(60) Provisional application No. 62/110,866, filed on Feb. 2, 2015.

(51) Int. Cl.
*A61F 2/70* (2006.01)
*A61H 3/00* (2006.01)

(52) U.S. Cl.
CPC .............. *A61F 2/70* (2013.01); *A61H 3/00* (2013.01); *A61F 2002/701* (2013.01); *A61F 2002/704* (2013.01)

(58) Field of Classification Search
None
See application file for complete search history.

(56) References Cited

U.S. PATENT DOCUMENTS

2014/0340301 A1\* 11/2014 Clement ................ G06F 3/014
345/156

FOREIGN PATENT DOCUMENTS

| JP | 2009112448 A | \* | 5/2009 |
|----|--------------|---|--------|
| JP | 2010162064 A |   | 7/2010 |
| JP | 2011110070 A |   | 6/2011 |
| JP | 2012024201 A |   | 2/2012 |
| JP | 2012045251 A | \* | 3/2012 |
| JP | 2014087636 A | \* | 5/2014 |

OTHER PUBLICATIONS

Extended Search Report regarding related EP App. No. 16153682.6; dated Jun. 9, 2016; 112 pgs.

\* cited by examiner

*Primary Examiner* — Thienvu V Tran
*Assistant Examiner* — David M Stables

(57) ABSTRACT

A human exoskeleton is provided and includes a power source. The human exoskeleton also includes a controller configured to activate power between the exoskeleton and the power source. The human exoskeleton further includes a power disconnect mechanism electronically connected to the controller and configured to disconnect power between the exoskeleton and the battery when activated, the power disconnect mechanism physically in contact with a wearer of the human exoskeleton.

11 Claims, 4 Drawing Sheets

USER CONTROLLED POWER DISCONNECT MECHANISM FOR HUMAN EXOSKELETON

CROSS-REFERENCE TO RELATED APPLICATION

This patent application claims priority to U.S. Provisional Patent Application Ser. No. 62/110,866, filed Feb. 2, 2015, which is incorporated herein by reference in its entirety.

BACKGROUND

Traditionally there are multiple people involved in the operation of a human assist exoskeleton, including the wearer, the controller, and the spotters. The idea is having more people aware and responsible for the exoskeleton's movement in attempt to keep the wearer of the exoskeleton from falling. Sometimes the wearer and the controller are the same person but this is not always the case.

When using an exoskeleton the wearer should be able to rapidly stop the test if they feel unsafe or uncomfortable. A manual push-button, separate from the exoskeleton and accessible by the human controller is often implemented in the design. Another power disconnect option is to physically unplug the exoskeleton via an external power cord. These methods have relied on a proactive action in order to stop operation.

This introduces a delayed reaction time into the disconnect procedure. In the event that the wearer feels a test needs to be stopped before it is apparent to the controller, there will be a delay in relaying the information from one person to the other. Additionally, the proactive action of pushing a button to stop power takes longer than a reactive action.

In other implementations, the wearer must hold a railing or similar device. The contact with the railing enables motion by closing a circuit. If the wearer lets go—i.e., breaks the circuit—power is interrupted and the exoskeleton ceases movement.

SUMMARY

According to one aspect of the invention, a human exoskeleton is provided and includes a power source. The human exoskeleton also includes a controller configured to activate power between the exoskeleton and the power source. The human exoskeleton further includes a power disconnect mechanism electronically connected to the controller and configured to disconnect power between the exoskeleton and the battery when activated, the power disconnect mechanism physically in contact with a wearer of the human exoskeleton.

According to another aspect of the invention, a power disconnect mechanism for a human exoskeleton is provided. The power disconnect mechanism includes an interface secured to a hand of a wearer of the human exoskeleton. The power disconnect mechanism also includes a controller in operative communication with the interface and configured to activate power between the human exoskeleton and a power source, the interface disconnecting power between the human exoskeleton and the power source when activated.

These and other advantages and features will become more apparent from the following description taken in conjunction with the drawings.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION

Referring now to the Figures, where the invention will be described with reference to specific embodiments, without limiting same, the embodiments described herein will remedy issues associated with operation of an exoskeleton by utilizing a power disconnect mechanism held or contacted by a wearer of the exoskeleton. In embodiments of the invention, the mechaism strategically uses natural human reaction under stress to disconnect power to the exoskeleton. Thus, direct control of the exoskeleton is given to the wearer/user with a reactive action solution. This will be described in greater detail hereinafter.

Figure 1:
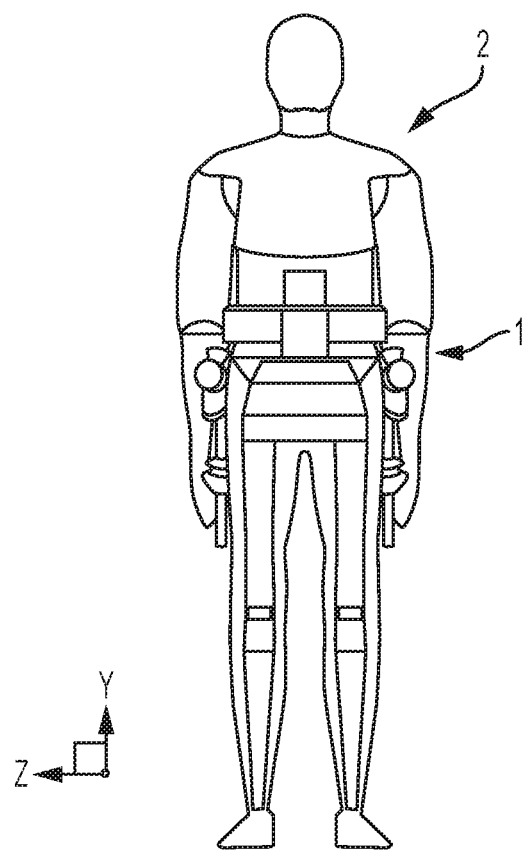
FIG. 1 illustrates an exoskeleton of the invention.
Figure 2:
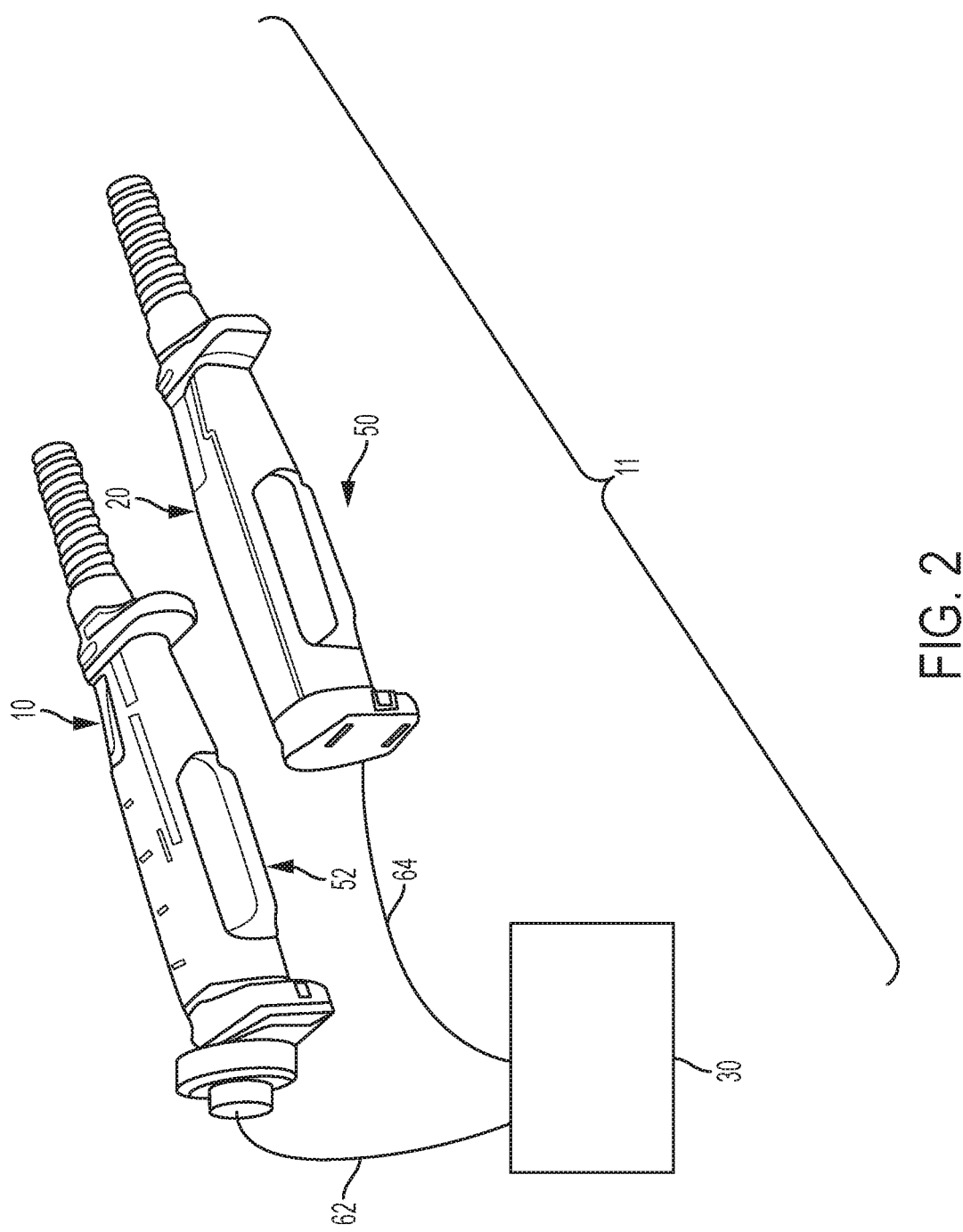
FIG. 2 illustrates a power disconnect mechanism according to an aspect of the invention.
Figure 3:
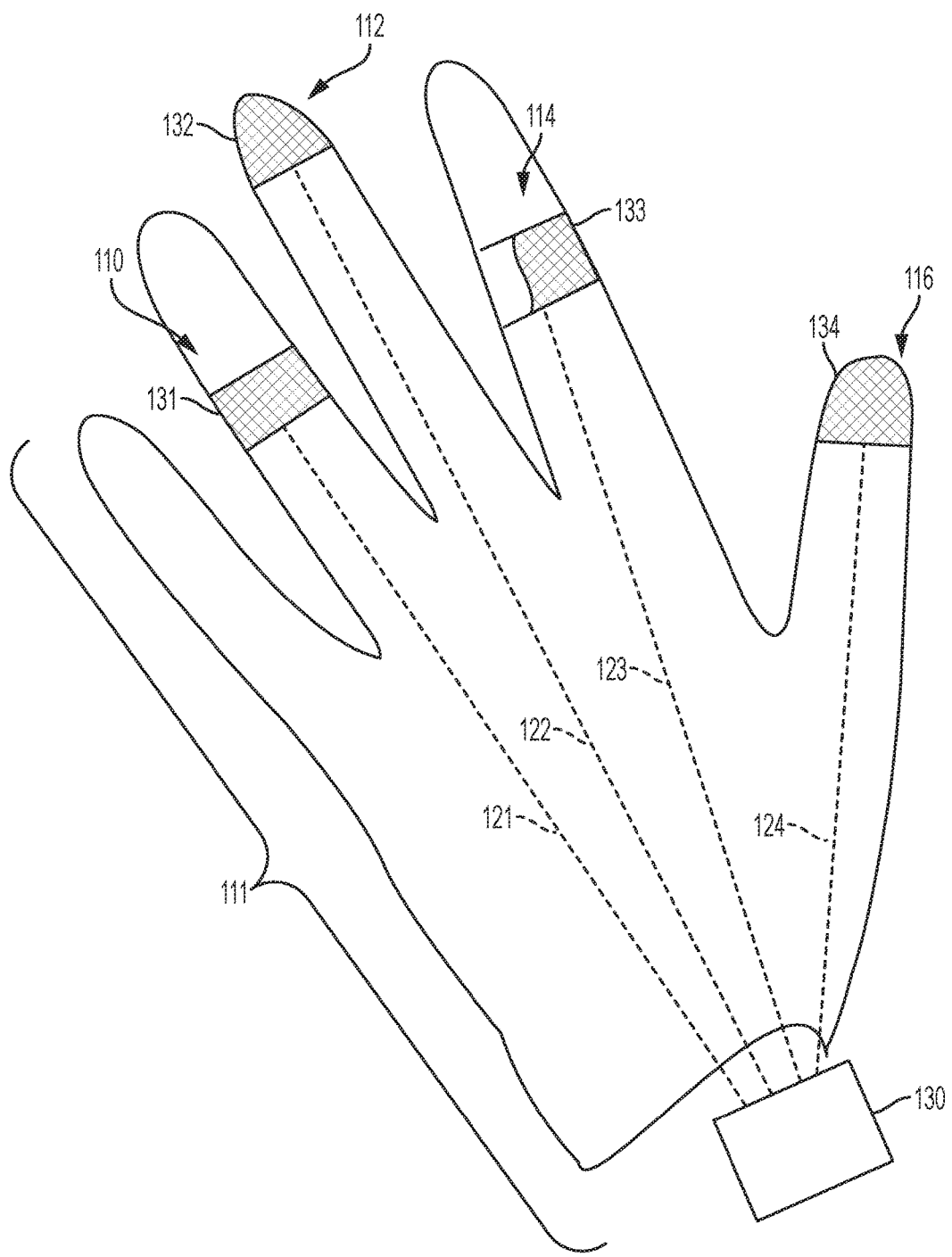
FIG. 3 illustrates the power disconnect mechanism according to another aspect of the invention.
Figure 4:
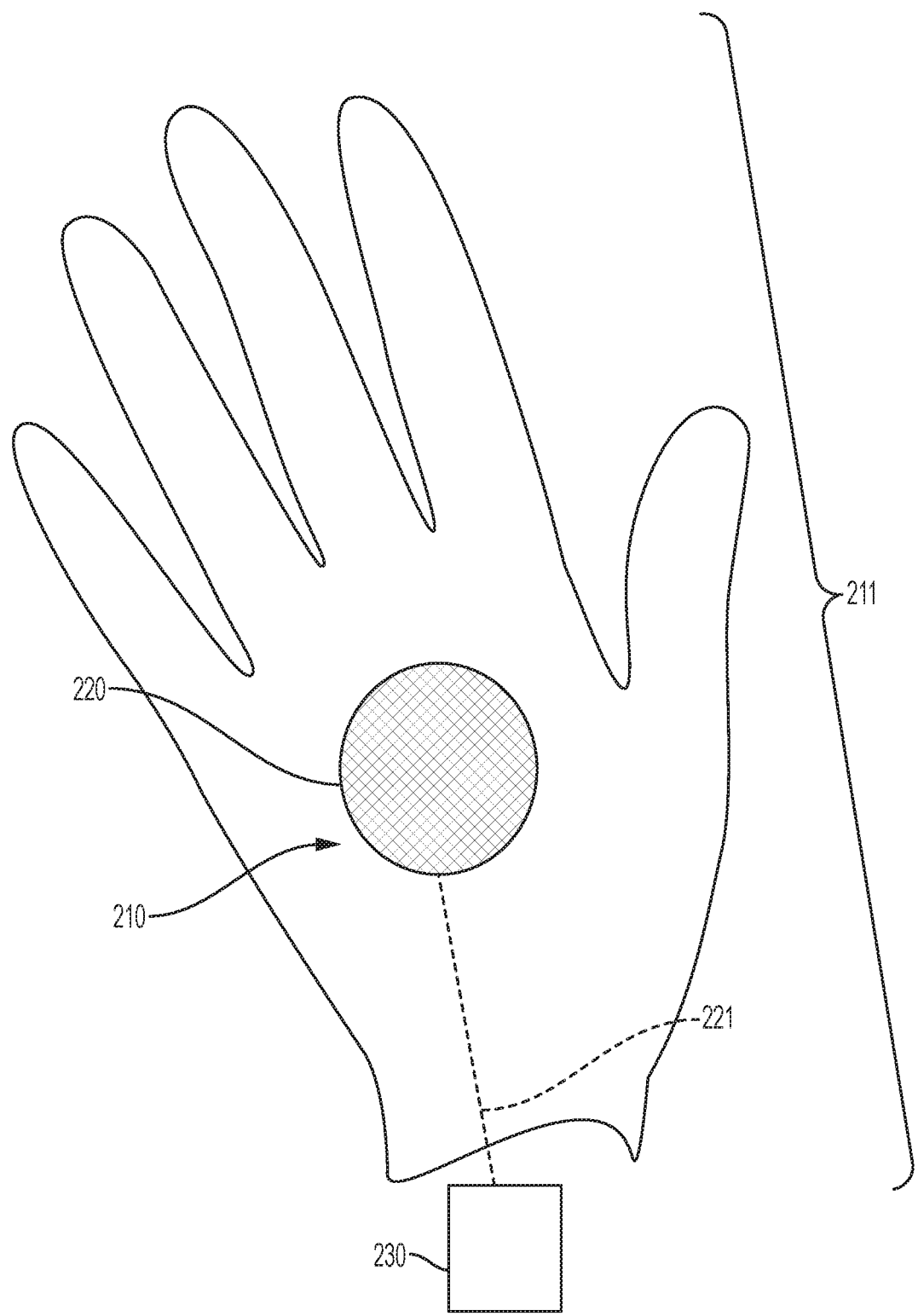
FIG. 4 illustrates the power disconnect mechanism according to another aspect of the invention.

FIG. 1 illustrates an exoskeleton 1 to be worn by a user 2 (referred to interchangeably herein as a wearer 2). Multiple embodiments of an exoskeleton 1, and more particularly a power disconnect mechanism, are shown in FIGS. 2-4. The power disconnect mechanism enabled by a controller is shown in FIGS. 2-4, the embodiments of the power disconnect mechanism including components referenced with numerals 10, 12 (FIG. 2), 110, 112, 114, 116 (FIG. 3), and 210 (FIG. 4), each of which described in detail herein. Each of the power disconnect mechanism embodiments disconnect power from a power source under certain conditions associated with a "fight" and/or "flight" response of the user 2. The embodiments utilize natural human reactions when confronted with the potential of falling, imminent collision, or other perceived threats. The reaction utilized is the natural instinct to hold up and open the hands as if to brace for a fall or alternatively clench up. Safety switch(es) of the power disconnect mechanism will be connected to the main power of the exoskeleton 1 which includes a main control board, motor control boards and sensors.

As shown in FIG. 2, a power disconnect mechanism 11 includes two hand grips 10, 20 that are ergonomically fitted to be held by the user 2 of the exoskeleton 1. The user 2 holds the hand grips 10, 20 in the palm of each hand. If the user clenches the hand grips 10, 20 too tightly, or throws up their hands in an open palm maneuver, thus releasing their grip, a disconnect signal is activated. More particularly, the user 2 holds switches 50, 52, individually in one embodiment and collectively in another embodiment, to maintain closure of a circuit to maintain exoskeleton power. Release and/or over-pressing the switches 50, 52 will open a circuit by sending a signal through wires 62, 64 and cause power from a power source 30 to be disconnected from exoskeleton 1. In one embodiment power source 30 may be a battery or battery pack. In other embodiments, power source 30 may include a main control board or board(s) and various sensors enabling operation of the exoskeleton 1. In one embodiment, wires 62, 64 may eliminated in favor of a wireless connection between switches 50, 52 and power source 30.

As shown in FIG. 3, power disconnect mechanism 111 is another embodiment. In the illustrated embodiment, any one finger—or multiple fingers as shown—are fitted with conductive pads 110, 112, 114 and/or 116. Each of conductive pads 110, 112, 114 and 116 are attached to a finger, thumb or hand (as shown) of the wearer 2 of the exoskeleton 1. Each conductive pad 110, 112, 114, 116 is electronically connected to a power source 130, which may be a battery or battery pack. In other embodiments, power source 130 may include a main control board or board(s) and various sensors enabling operation of the exoskeleton 1. It will be appreciated that the connection may be wires 121, 122, 123 or 124 or may alternatively be wirelessly connected. In one embodiment, the pads 110, 112, 114 and 116 are fitted with a pressure sensitive switch 131, 132, 133, 134 which—when depressed—sends a signal to disconnect power between power source 130 and exoskeleton 1.

Multiple embodiments of that shown in FIG. 3 are contemplated. The pads 110, 112, 114 and 116 are attached to the user with adhesives, hook and loop fasteners or the like. Only one or any combination of the multiple pads 110, 112, 114, 116 may be used in various combinations. In addition, it is contemplated that the contacting of two of the pads 110, 112, 114 and 116 together opens the circuit between power source 130 and exoskeleton 1.

As best shown in FIG. 4, power disconnect mechanism 211 includes a pressure sensitive pad 210. As shown, it is contemplated that the clenching of a fist will activate the switch 220 to open the circuit between power source 230 and exoskeleton 1. In an alternative embodiment, it is contemplated that a finger touch to the palm of the hand having the pad 210 will activate the switch and open the circuit between power source 230 and exoskeleton 1. Like the embodiments of FIGS. 2 and 3, conductive pad 210 is electronically connected to the power source 230, which may be a battery or battery pack. In other embodiments, power source may include a main control board or board(s) and various sensors enabling operation of the exoskeleton 1. It will be appreciated that the connection wire 221 may be hard wired to the power source 230 or may eliminated in favor of a wireless connection.

The embodiments described herein give the wearer 2 a greater amount of control of the exoskeleton 1, increasing the sense of safety and control of the user 2 and enhancing safety and reliability of the exoskeleton 1.

It is to be understood that the power disconnect mechanisms 11, 111, 211 described herein (i.e., switches and pads) can cut power either when released or over-pressed in some embodiments. Alternatively, some embodiments rely on only one of release and over-pressure. In an embodiment that disconnects power when released or over-pressed, the controller is programmed with a range of pressure that allows the human exoskeleton to be powered. It is only within the programmed range that the human exoskeleton 1 is powered. A pressure applied to an interface of the power disconnect mechanism below the range (e.g., release by user) or a pressure applied above the range deactivates power of the human exoskeleton.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description.

Having thus described the invention, it is claimed:

1. A human exoskeleton comprising
a power source;
a controller configured to activate power between the exoskeleton and the power source; and
a power disconnect mechanism electronically connected to the controller and configured to disconnect power between the exoskeleton and the power source when activated, the power disconnect mechanism being a pair of hand grips, each of the hand grips having a respective switch physically in contact with a wearer of the human exoskeleton, the power disconnect mechanism activated when a pressure applied to the power disconnect mechanism is above a range programmed in the controller or below the range programmed in the controller, the human exoskeleton powered only when the pressure applied to the power disconnect mechanism is within the range programmed in the controller.

2. The human exoskeleton of claim 1, wherein the power disconnect mechanism comprises a conductive pad.

3. The human exoskeleton of claim 2, wherein the power disconnect mechanism comprises a plurality of conductive pads, the power disconnect mechanism activated when the conductive pads contact each other.

4. The human exoskeleton of claim 1, wherein the power disconnect mechanism comprises a pressure sensitive pad.

5. The human exoskeleton of claim 1, wherein the power disconnect mechanism is secured to a palm of the wearer.

6. The human exoskeleton of claim 1, wherein the power disconnect mechanism is activated when depressed.

7. A power disconnect mechanism for a human exoskeleton comprising:
an interface secured to a hand of a wearer of the human exoskeleton, the interface being a pair of hand grips, each of the hand grips having a respective switch; and
a controller in operative communication with the interface and configured to activate power between the human exoskeleton and a power source, the interface disconnecting power between the human exoskeleton and the power source when activated, the power disconnect mechanism activated when a pressure applied to the power disconnect mechanism is above a range programmed in the controller or below the range programmed in the controller, the human exoskeleton powered only when the pressure applied to the power disconnect mechanism is within the range programmed in the controller.

8. The power disconnect mechanism of claim 7, wherein the interface is in wired communication with the controller.

9. The power disconnect mechanism of claim 7, wherein the interface is in wireless communication with the controller.

10. The power disconnect mechanism of claim 7, wherein the power disconnect mechanism comprises a conductive pad.

11. The power disconnect mechanism of claim 7, wherein the power disconnect mechanism comprises a pressure sensitive pad.

* * * * *